United States Patent
Polster

(10) Patent No.: US 9,326,754 B2
(45) Date of Patent: May 3, 2016

(54) METHOD AND APPARATUS FOR TISSUE SAMPLING

(75) Inventor: Joshua M. Polster, Shaker Heights, OH (US)

(73) Assignee: The Cleveland Clinic, Cleveland, OH (US)

(*) Notice: Subject to any disclaimer, the term of this patent is extended or adjusted under 35 U.S.C. 154(b) by 728 days.

(21) Appl. No.: 12/743,427

(22) PCT Filed: Nov. 20, 2008

(86) PCT No.: PCT/US2008/084192
§ 371 (c)(1),
(2), (4) Date: May 18, 2010

(87) PCT Pub. No.: WO2009/079155
PCT Pub. Date: Jun. 25, 2009

(65) Prior Publication Data
US 2010/0280407 A1 Nov. 4, 2010

Related U.S. Application Data

(60) Provisional application No. 60/989,268, filed on Nov. 20, 2007.

(51) Int. Cl.
*A61B 10/02* (2006.01)
*A61B 17/3205* (2006.01)
(Continued)

(52) U.S. Cl.
CPC ......... *A61B 10/0275* (2013.01); *A61B 10/0266* (2013.01); *A61B 10/0283* (2013.01); *A61B 17/32053* (2013.01); *A61B 2010/0208* (2013.01); *A61B 2017/32004* (2013.01); *A61B 2017/320791* (2013.01); *A61B 2017/3409* (2013.01); *A61B 2019/305* (2013.01); *A61B 2019/462* (2013.01)

(58) Field of Classification Search
CPC .......... A61B 10/0266; A61B 10/0275; A61B 10/0283; A61B 17/32053; A61B 2010/0208; A61B 2017/320791; A61B 2019/305; A61B 2019/462
USPC .................. 600/564–568; 606/167, 170, 172
See application file for complete search history.

(56) References Cited

U.S. PATENT DOCUMENTS 2,850,007 A 9/1958 Lingley
5,301,684 A * 4/1994 Ogirala .......................... 600/567
(Continued)

FOREIGN PATENT DOCUMENTS

EP 0 829 239 A1 3/1998

*Primary Examiner* — Linda Dvorak
*Assistant Examiner* — Emily Lloyd
(74) *Attorney, Agent, or Firm* — Tarolli, Sundheim, Covell & Tummino LLP

(57) ABSTRACT

A tissue sampling device includes a sheath having an inner surface having a proximal end and a distal end, and an inner surface defining a passage. An inner tube is disposed within the passage. The inner tube has an inner surface defining a passage, and an outer surface radially spaced outward from the inner surface. A cutting needle is pivotally mounted to the inner tube and pivots between a first position radially inward of the inner surface of the sheath and a second position substantially radially outward of the outer surface of the inner tube. Relative movement between the inner tube and the sheath causes the cutting needle to move between the first position and the second position. Rotation of the inner tube relative to the sheath when the cutting needle is in the second position causes the cutting needle to remove tissue in a helical path.

20 Claims, 9 Drawing Sheets

(51) Int. Cl.
  *A61B 17/32* (2006.01)
  *A61B 17/3207* (2006.01)
  *A61B 17/34* (2006.01)
  *A61B 19/00* (2006.01)

(56) References Cited

U.S. PATENT DOCUMENTS

| | | | |
|---|---|---|---|
| 5,456,267 A * | 10/1995 | Stark | 128/898 |
| 5,660,186 A | 8/1997 | Bachir | |
| 6,136,014 A | 10/2000 | Sirimanne et al. | |
| 6,344,026 B1 | 2/2002 | Burbank et al. | |
| 6,488,636 B2 | 12/2002 | Bryan et al. | |
| 6,699,206 B2 | 3/2004 | Burbank et al. | |
| 6,846,292 B2 * | 1/2005 | Bakry | 600/564 |
| 6,849,080 B2 | 2/2005 | Lee et al. | |
| 7,329,267 B2 * | 2/2008 | Weber | 606/170 |
| 7,740,597 B2 * | 6/2010 | Cicenas et al. | 600/566 |
| 8,814,882 B2 * | 8/2014 | Oostman et al. | 600/564 |
| 2002/0115943 A1 | 8/2002 | Burbank et al. | |
| 2007/0142852 A1 | 6/2007 | Lee et al. | |

* cited by examiner

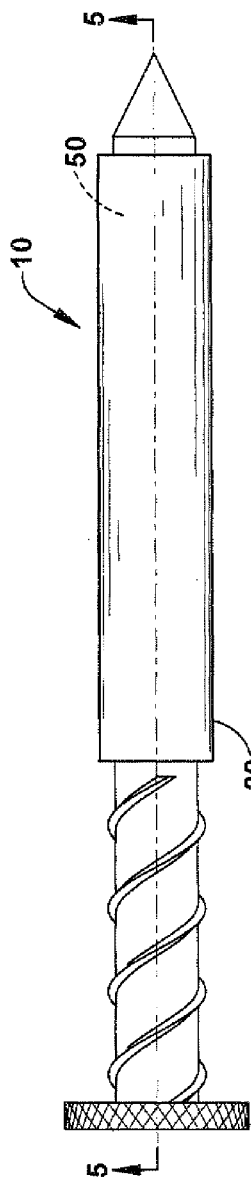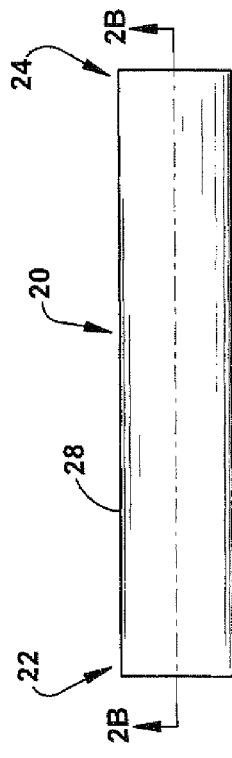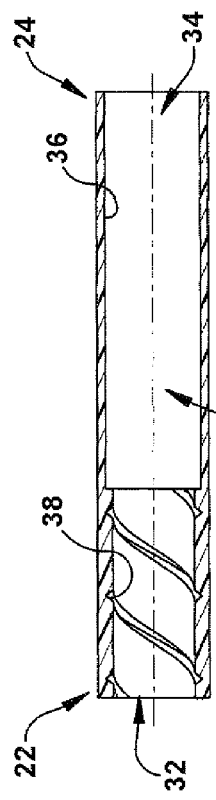

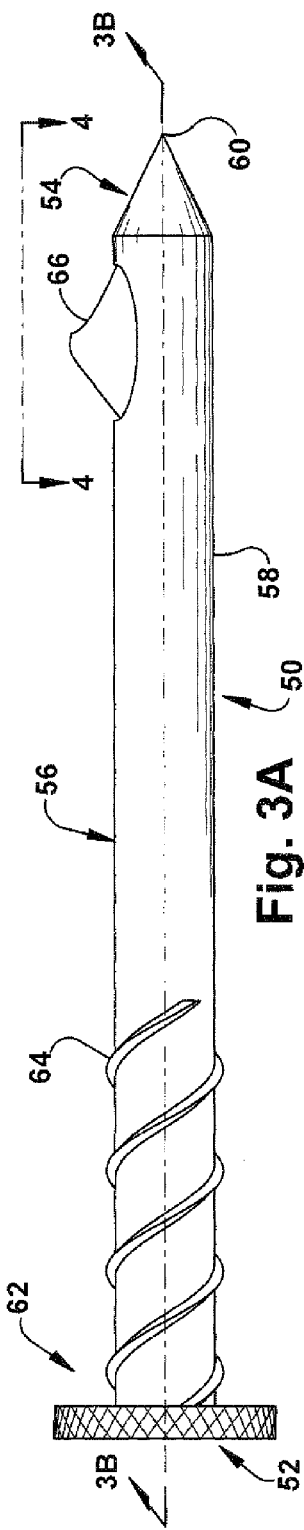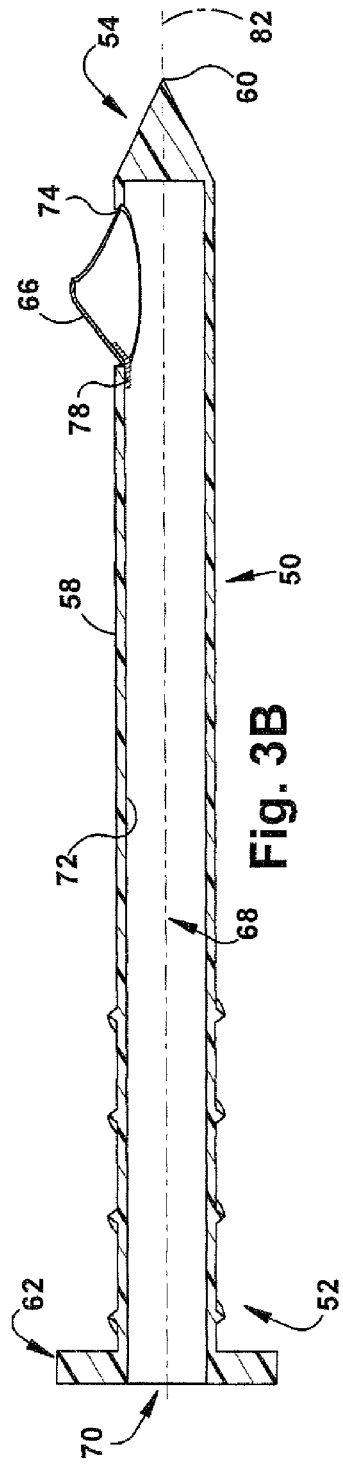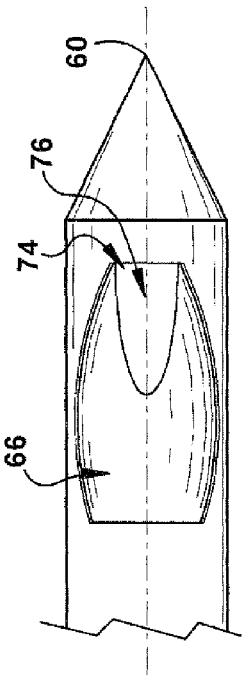

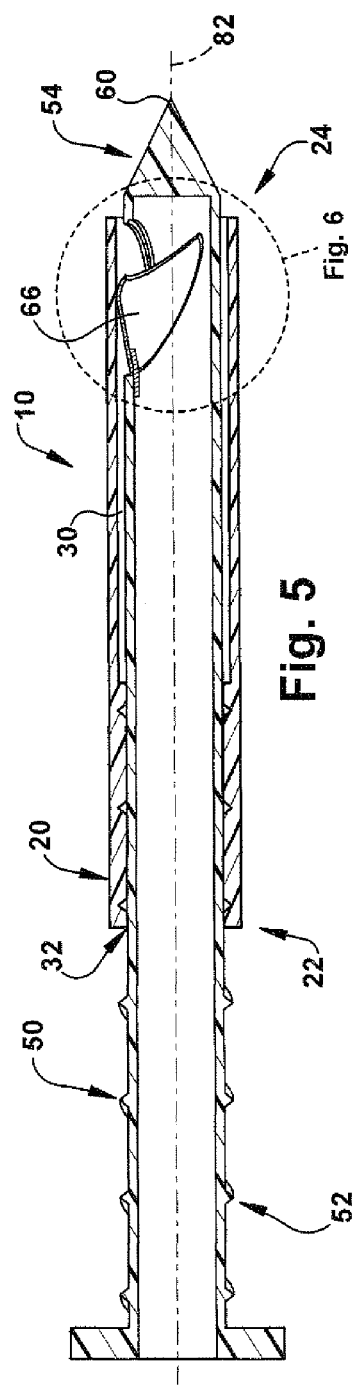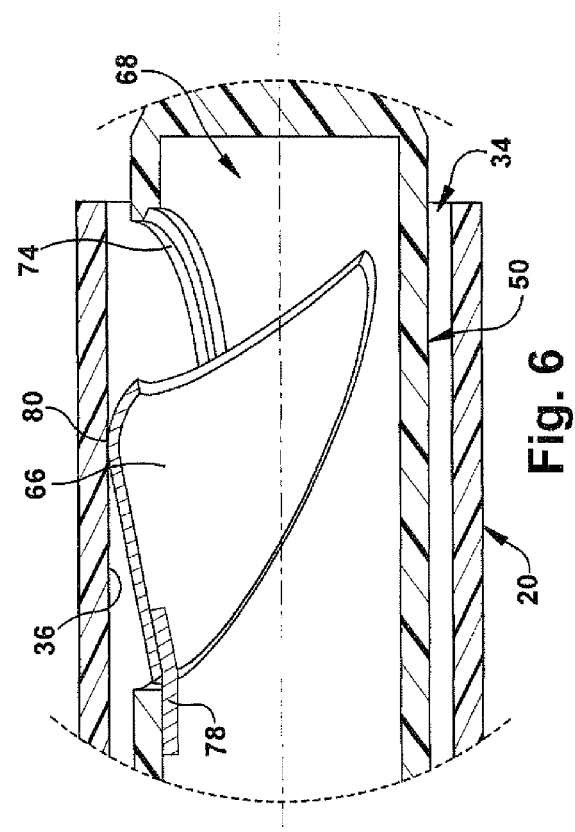

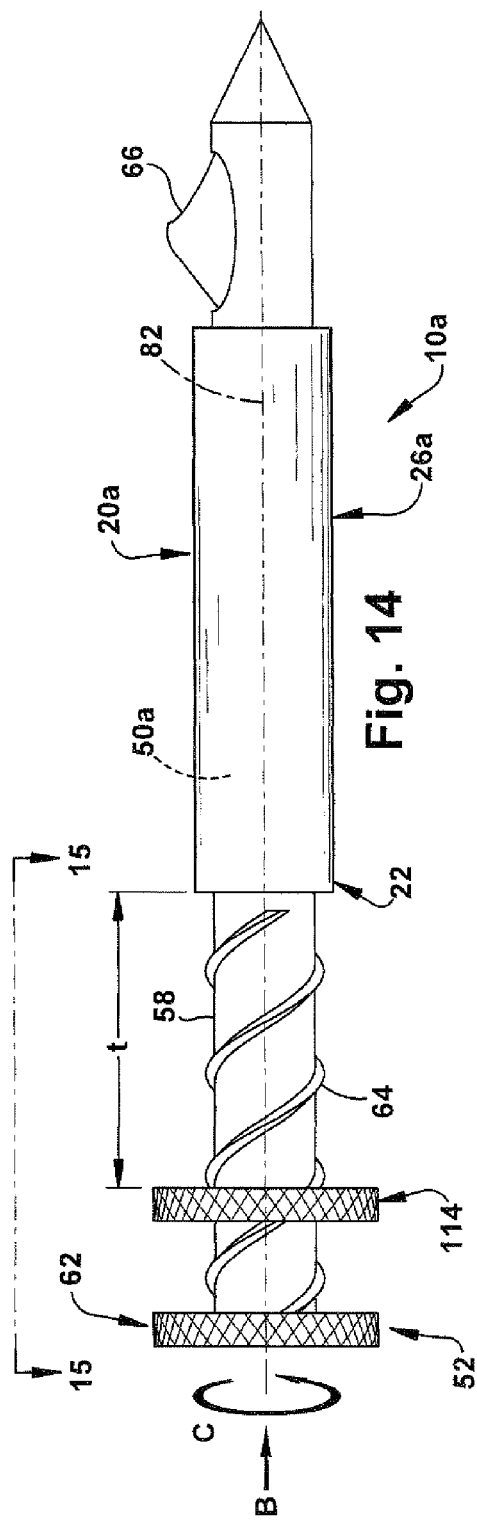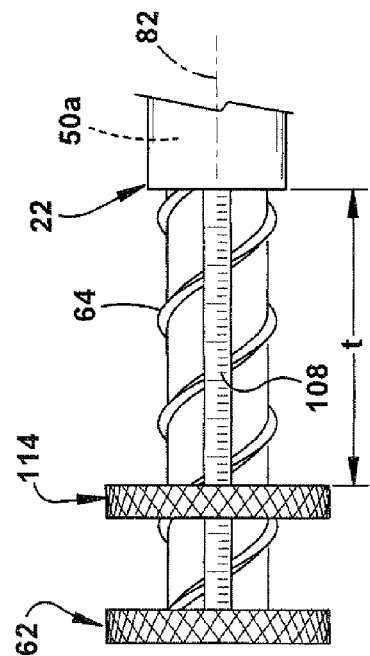

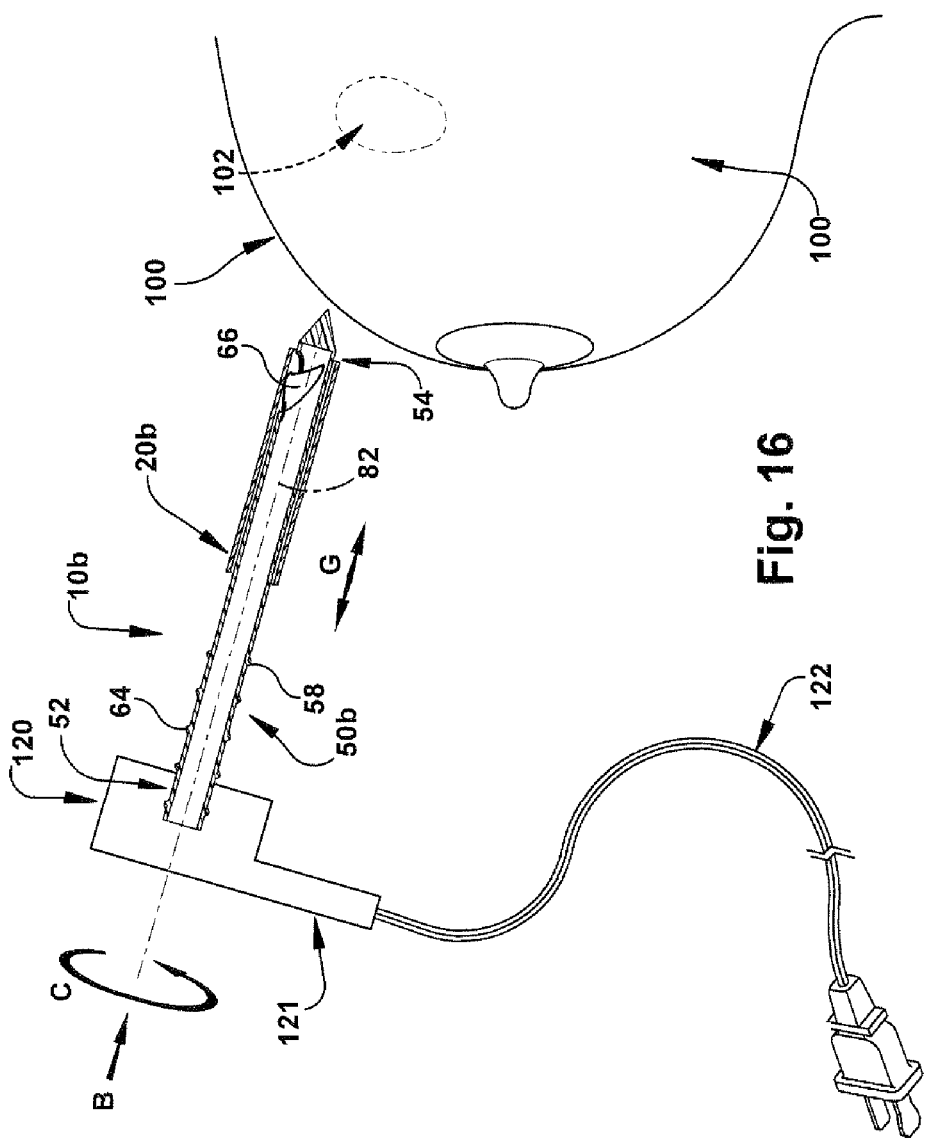

METHOD AND APPARATUS FOR TISSUE SAMPLING

RELATED APPLICATION

This application claims priority from U.S. Provisional Application No. 60/989,268, filed Nov. 20, 2007, the subject matter of which is incorporated herein by reference.

GOVERNMENT RIGHTS

The invention described in this application was supported, at least in part, by United States Government Contract No. W81XWH-05-1-0564 with the United States Department of Defense Telemedicine and Advanced Technology Research Center (TATRC) and, thus, the United States government may have certain rights in the invention.

TECHNICAL FIELD

The present invention is directed to a tissue sampling device, and in particular, to a biopsy device that cuts tissue from a target area in the body along a helical path.

BACKGROUND OF THE INVENTION

Cancer is one of the leading causes of death in the United States. Several hundred thousand individuals die as a result of some form of cancer. Therefore, the need to diagnose and treat cancerous or otherwise harmful lesions at the earliest stage possible is highly coveted. Frequently, areas of the body may arouse suspicion as being or becoming cancerous due to a change in appearance, function, or physiology. Alternatively, one's familial history and/or lifestyle may lead a physician to believe that individual is more susceptible or likely to get cancer in a particular part of the body.

Testing the suspicious or otherwise targeted tissue for cancerous growths and/or indicia is commonly done by taking a sample or specimen of the tissue in a procedure called a biopsy. The tissue sample is removed from the body and diagnostic tests are performed on it to deduce its propensity for, or the presence of, malignant cell growth. A biopsy is commonly performed by inserting a needle into the targeted area along a straight path. The needle cuts the tissue sample and simultaneously collects it such that the sample can be removed from the body. A problem with cutting tissue samples along a straight path is that multiple samples (passes) must be taken in the targeted area to obtain a sufficient tissue volume for diagnostic testing. This can be both time consuming as well as uncomfortable for the patient, as acquiring multiple tissue samples requires multiple needle insertions. Additionally, the depth of the tissue sample taken is frequently a function of the length of the needle cutting edge and, thus, is approximated instead of closely monitored. Therefore, there is a need for a tissue sampling device capable of acquiring larger volumes of tissue within one pass to reduce the time of the procedure and discomfort to the patient. There is also a need to closely monitor the depth of the tissue sample acquired to ensure that only tissue from the targeted area, i.e., the abnormal tissue, is removed.

SUMMARY OF THE INVENTION

The present invention is directed to a tissue sampling device for removing tissue from a target area in the body. The device includes a sheath having a proximal end, a distal end, and an inner surface extending between the proximal end and the distal end and defining a passage. An inner tube is disposed within the passage of the sheath. The inner tube has a first end, a second end, an inner surface extending between the first end and the second end and defining a passage, and an outer surface spaced radially outward from the inner surface. A cutting needle is pivotally mounted to the inner tube. The cutting needle pivots between a first position radially inward of the inner surface of the sheath and a second position substantially radially outward of the outer surface of the inner tube. Relative movement between the inner tube and the sheath causes the cutting needle to move between the first position and the second position. Rotation of the inner tube relative to the sheath when the cutting needle is in the second position causes the cutting needle to remove tissue in a helical path.

The present invention is also directed to a method of tissue sampling from a target area in the body. The method comprises the step of providing a sheath having a proximal end, a distal end, and an inner surface extending between the proximal end and the distal end and defining a passage. An inner tube is provided within the passage of the sheath. The inner tube has a first end, a second end, an inner surface extending between the first end and the second end and defining a passage, and an outer surface spaced radially outward from the inner surface. A cutting needle is pivotally mounted to the inner tube, the cutting needle pivoting between a first position and a second position, the first position being radially inward of the inner surface of the sheath and the second position being substantially radially outward of the outer surface of the inner tube. The sheath is slid relative to the inner tube to pivot the cutting needle from the first position to the second position. Tissue is removed from the target area along a helical path by rotating the inner tube.

BRIEF DESCRIPTION OF THE DRAWINGS

The foregoing and other features and advantages of the present invention will become apparent to those skilled in the art to which the present invention relates upon reading the following description with reference to the accompanying drawings, in which:

FIG. 1 is a side elevational view of a tissue sampling device in accordance with an exemplary embodiment of the present invention;

FIG. 2A is a side elevational view of a sheath of FIG. 1;

FIG. 2B is a section view of the sheath of FIG. 2A taken along line 2B-2B;

FIG. 3A is a side elevational view of an inner tube of FIG. 1;

FIG. 3B is a section view of the inner tube taken along line 3B-3B in FIG. 3A;

FIG. 4 is a top view of the inner tube taken along line 4-4 in FIG. 3A;

FIG. 5 is a section view of the tissue sampling device taken along line 5-5 in FIG. 1;

FIG. 6 is an enlarged view of a cutting needle of FIG. 5;

FIG. 14 is a side view of an alternative embodiment of the present invention;

FIG. 15 is a top view of the device of FIG. 14; and

FIG. 16 is a side view of an alternative embodiment of the present invention.

DETAILED DESCRIPTION

Figure 8:
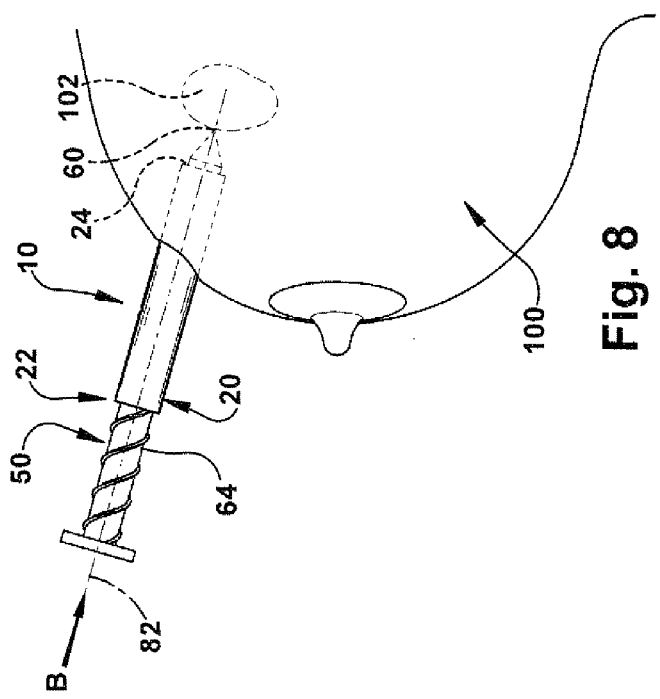
FIG. 8 is a schematic illustration of the device penetrating the breast.

The present invention is directed to a tissue sampling device, and in particular, to a biopsy device that cuts tissue from a target area in the body along a helical path. As shown in FIG. 1, the device 10 includes an outer sheath 20 and a concentric inner tube 50. The sheath 20 has a proximal end 22, a distal end 24, and a body portion 26 extending between the proximal end and the distal end (FIG. 2A). The distal end 24 may be blunt or have an otherwise atraumatic construction. The sheath 20 further includes an outer surface 28 and a substantially concentric inner surface 36, thereby forming a generally tubular cross-section (FIG. 2B). Although the inner surface 36 and the outer surface 28 are illustrated as having circular cross-sections, those having ordinary skill will appreciate that the inner and outer surfaces can have alternative cross-sections, such as triangular, square or any other polygonal construction. The inner surface 36 defines a passage 30, which extends from an opening 32 in the proximal end 22 to an opening 34 in the distal end 24 (FIG. 2B). The inner surface 36 at the proximal end 22 includes internal threads 38 that extend from the proximal end towards the distal end 24. The threads 38 may be square, helical, or the like. The sheath 20 may be made out of metal, plastic, ceramic or combinations thereof or otherwise any suitable biocompatible material.

The inner tube 50 is illustrated in FIGS. 3A-4. The inner tube 50 extends along a central axis 82 and includes a first end 52, a second end 54, and a body portion 56 extending between the first end and the second end. The first end 52 may include a handle 62 or other means ergonomically designed for grasping. The second end 54 includes a pointed or sharpened tip 60 configured to penetrate skin and soft tissue. The inner tube 50 further includes an inner surface 72 and a substantially concentric outer surface 58, thereby forming a generally tubular cross-section about the central axis 82. Although the inner surface 72 and the outer surface 58 are illustrated as having circular cross-sections, those having ordinary skill will appreciate that the inner and outer surfaces can have alternative cross-sections, such as triangular, square or any other polygonal construction. Regardless of the particular construction, the inner tube 50 is sized to fit within the passage 30 of the sheath 20. The inner tube 50 may be made out of metal, plastic, ceramic or combinations thereof or otherwise any suitable biocompatible material.

The outer surface 58 extends from the first end 52 to the second end 54 and includes external threads 64 that extend from the first end towards the second end. The threads 64 may be square, helical or otherwise configured to releasably engage the internal threads 38 on the sheath 20. The inner surface 72 defines an inner passage 68 that extends from an opening 70 in the first end 52 towards the second end 54 but terminates prior to the second end. The second end 54 includes a lateral opening 74 that extends from the outer surface 58 to the inner surface 72, thereby placing the lateral opening in fluid communication with the passage 68. A cutting needle 66 is secured to the inner surface 72 and or the outer surface 58 of the inner tube 50 such that the cutting needle is positioned within the opening 74. Although the cutting needle 66 is illustrated as having a substantially triangular cross-section, those having ordinary skill will appreciate that the cutting needle may exhibit any cross-section, such as circular, square, spherical, or may be otherwise configured to cut tissue. The cutting needle 66 includes an aperture 76 (FIG. 4) extending entirely therethrough that is in fluid communication with the passage 68 of the inner tube 50.

As shown, the cutting needle 66 is secured to the inner surface 72 via a hinge 78. This connection allows the cutting needle 66 to pivot about the hinge 78 and in the opening 74 relative to the inner tube 50. The hinge 78 has a bias which forces the cutting needle 66 substantially radially outward of the outer surface 58 and away from the passage 68. Although a hinge 78 is illustrated, those having ordinary skill in the art will appreciate that any alternative means of pivoting and/or connecting the cutting needle 66 to the inner tube 50 may be utilized.

The device 10 is shown in the assembled condition in FIG. 5. To assemble the device 10, the second end 54 of the inner tube 50 is inserted into the opening 32 at the proximal end 22 of the sheath 20. The second end 54 of the inner tube 50 is then fed through the passage 30 of the sheath 20 until the pointed tip 60 of the inner tube extends beyond the distal end of the sheath. In this configuration, the sheath 20 is substantially concentric with the inner tube 50 about the central axis 82 but the threads 38 on the sheath are not engaged with the threads 64 on the inner tube.

Due to the positioning of the cutting needle 66 and the bias of the hinge 78 in the radially outward direction, as the inner tube 50 is advanced through the passage 30 of the sheath 20, a portion 80 of the cutting needle 66 comes into contact with the inner surface 36 of the sheath (FIG. 6). Further advancement of the inner tube 50 causes the inner surface 36 to apply and maintain a radially inward force upon the portion 80 and, thus, upon the entire cutting needle 66. This inward force is sufficient to overcome the bias of the hinge 78, thereby causing the cutting needle 66 to pivot radially inward of the inner surface 36 of the sheath 20 and towards the central axis 82. The cutting needle 66 is thereby forced through the lateral opening 74 and into the passage 68 of the inner tube 50. The cutting needle 66 is maintained in this position so long as the inner surface 36 of the sheath 20 overlies and engages the cutting needle. This inward pivotal movement of the cutting needle 66 allows the second end 54 of the inner tube 50 to be advanced entirely through the passage 30 of the sheath 20.

Figure 7:
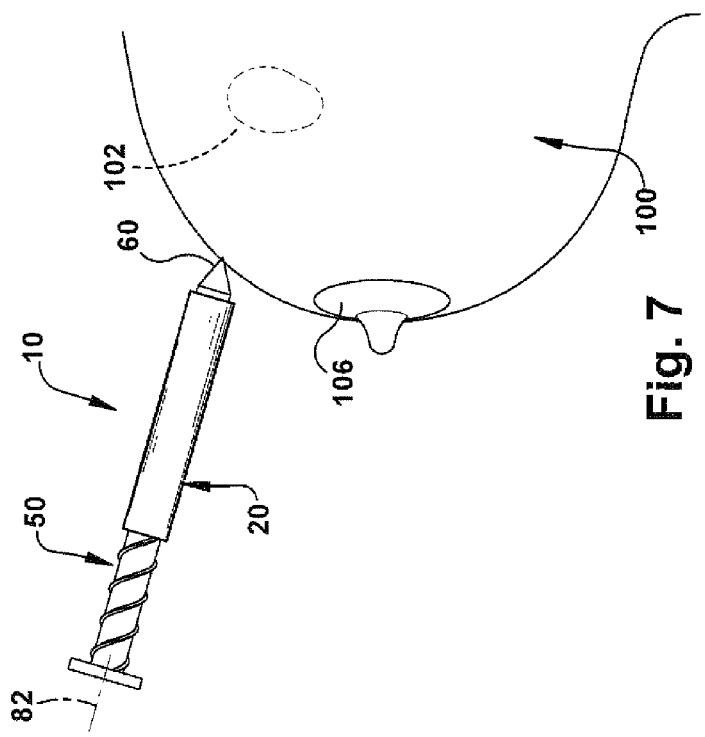
FIG. 7 is a schematic illustration of the device positioned on a breast.

Once the inner tube 50 is positioned within the sheath 20, the pointed tip 60 of the inner tube is placed on any portion of the body where a tissue sample is desired, such as a breast 100 (FIG. 7). The device 10 is positioned such that the central axis 82 of the inner tube 50 is aligned with a target area 102 of the breast tissue. The target area 102 may be tissue that is believed to be malignant or otherwise desired for diagnostic testing and/or observation. Although FIG. 7 illustrates that the device 10 is placed above the areola 106 of the breast 100, it should be understood that the device could be placed below the areola or anywhere else on the breast, depending on the location of the tissue sample desired.

The device 10 is then advanced into the breast 100 by imparting a force to the handle 62 on the inner tube 50 along the central axis 82 in the direction indicated at "B". The pointed tip 60 of the inner tube 50 facilitates penetration of the skin of the breast 100 and advancement into the underlying tissue towards the target area 102. When the inner tube 50 is pushed in the direction indicated at B, the inner tube slides longitudinally relative to the sheath 20 since the threads 64 on the inner tube are not engaged with the threads 38 on the sheath. The inner tube 50 is advanced into the tissue until the threads 64 on the inner tube 50, i.e., the thread farthest from the first end 52 of the inner tube, abut the proximal end 22 of the sheath 20 (FIG. 8). During this initial engagement, the inner surface 36 of the sheath 20 remains positioned over the cutting needle 66 such that the cutting needle is maintained radially inward of the inner surface of the sheath and within the passage 68 of the inner tube 50.

Continued advancement of the inner tube 50 causes the distal end 24 of the sheath 20 to engage the surface of the breast 100. The atraumatic nature of the distal end 24 of the sheath 20, however, prohibits it from penetrating the breast 100. Since the threads 64 of the inner tube 50 now abut the proximal end 22 of the sheath 20, the threads on the inner tube prevent the inner tube from sliding relative to the sheath and, thus, the force imparted upon the inner tube is likewise imparted upon the sheath. Accordingly, subsequent force applied to the inner tube 50 causes threads 64 on the inner tube to, in effect, push the proximal end 22 of the sheath 20, which causes the distal end 24 of the sheath to penetrate the skin and advance into the underlying tissue along with the pointed tip 60 of the inner tube. While the device 10 advances into the tissue, the cutting needle 66 remains radially inward of the inner surface 36 of the sheath 20.

Figure 9:
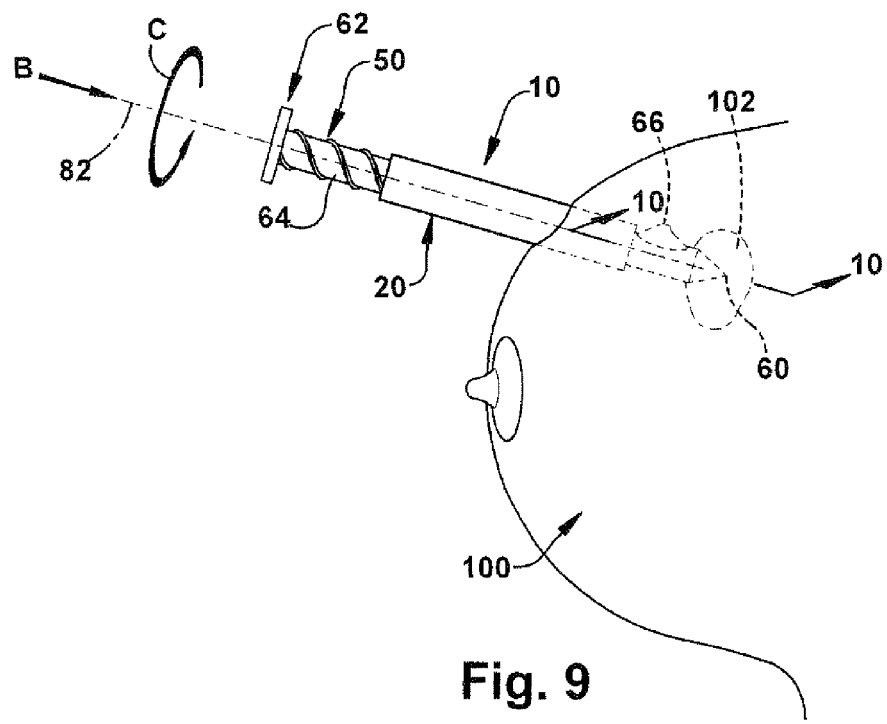
FIG. 9 is a schematic illustration of the device advancing further into the breast.

The pointed tip 60 of the inner tube 50 is advanced into the target area 102 by applying additional force to the inner tube in the direction B. Once the target area 102 is reached, the cutting needle 66 is extended and advanced to collect the tissue sample. In particular, the handle 62 on the first end 52 of the inner tube 50 is rotated clockwise, as indicated by "C" (FIG. 9). This rotation causes the threads 64 on the first end 52 of the inner tube 50 to engage the threads 38 on the proximal end 22 of the sheath 20. The surface tension between the outer surface 28 of the sheath 20 and the underlying breast tissue may be sufficient to maintain the sheath 20 in a rotationally and longitudinally fixed condition while the inner tube 50 is rotated, thereby allowing for threaded engagement between the sheath and the inner tube. It may be necessary, however, for the practitioner to hold the sheath 20 in place while the inner tube 50 is rotated to ensure that the inner tube and the sheath do not rotate together and, thus, that the threads 64 on the inner tube engage the threads 38 on the sheath.

Figure 10:
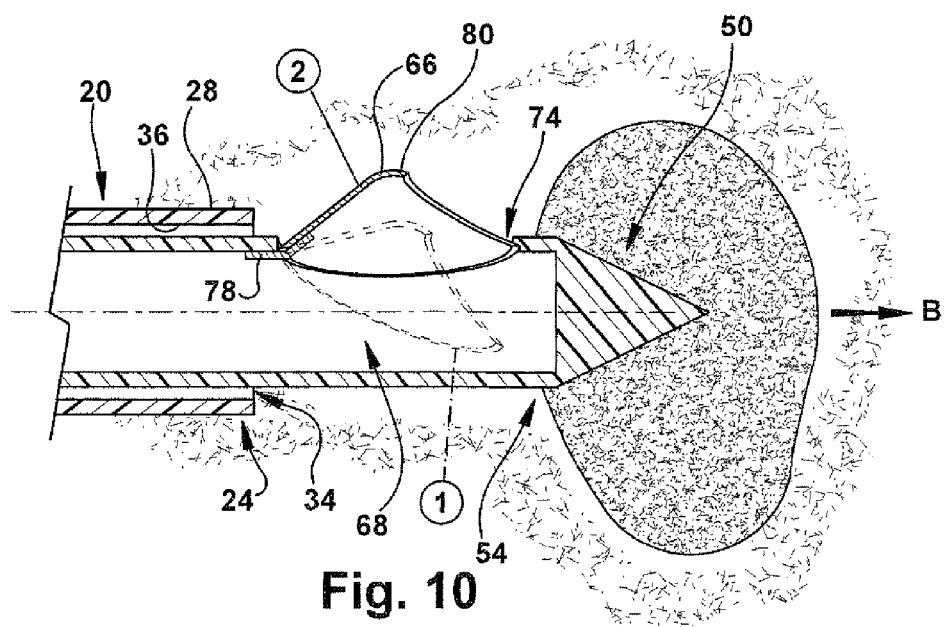
FIG. 10 is a section view of the device taken along line 10-10 in FIG. 9.

In any case, since the sheath 20 is stationary while the inner tube 50 is rotated, the threaded engagement between the sheath and the inner tube causes the rotating inner tube to advance in the direction indicated at B along the central axis 82 relative to the sheath. As shown in FIG. 10, movement in the direction indicated at B of the inner tube 50 relative to the sheath 20 causes the second end 54 of the inner tube and, thus, the cutting needle 66 in the lateral opening 74 to pass through and beyond the opening 34 in the distal end 24 of the sheath. Due to the length of the sheath 20 and the threads 38 and 64 on the sheath and the inner tube 50, respectively, the cutting needle 66 may not pass beyond the opening 34 in the distal end 24 of the sheath 20 until a predetermined number of threads on the sheath engage the threads on the inner tube.

Regardless, when the cutting needle 66 is passed through the opening 34 in the distal end 24 of the sheath 20, the cutting needle moves from a first position, indicated by "1" to a second position indicated by "2". As noted with regard to assembly of the device 10, in the first, retracted position, the cutting needle 66 is radially inward of the inner surface 36 of the sheath 20 and at least partially disposed within the passage 68 of the inner tube 50. The cutting needle 66 moves between the retracted and the extended positions under the influence of the bias of the hinge 78. In particular, since movement of the inner tube 50 causes the cutting needle 66 to advance past the distal end 24 of the sheath 20, the cutting needle is moved out of contact with the inner surface 36 of the sheath, i.e., the inner surface does not overlie the cutting needle. This removes the radially inward force previously exerted upon the portion 80 of the cutting needle 66 by the inner surface 36 of the sheath 20.

Upon removal of the force of the inner surface 36 of the sheath 20 upon the cutting needle 66, the biasing nature of the hinge 78 causes the cutting needle to pivot radially outwards from the central axis 82 and away from the passage 68 of the inner tube 50 to place the cutting needle in the second, extended position. In the extended position, the cutting needle 66 is in contact with the surrounding breast tissue and substantially radially outward of the outer surface 58 of the inner tube 50. The extent to which the cutting needle 66 extends radially beyond the outer surface 58 of the inner tube 50 correlates to the contact area between the cutting needle 66 and the breast tissue and, thus, influences the size of the cross-section of the tissue sample taken.

Figure 11:
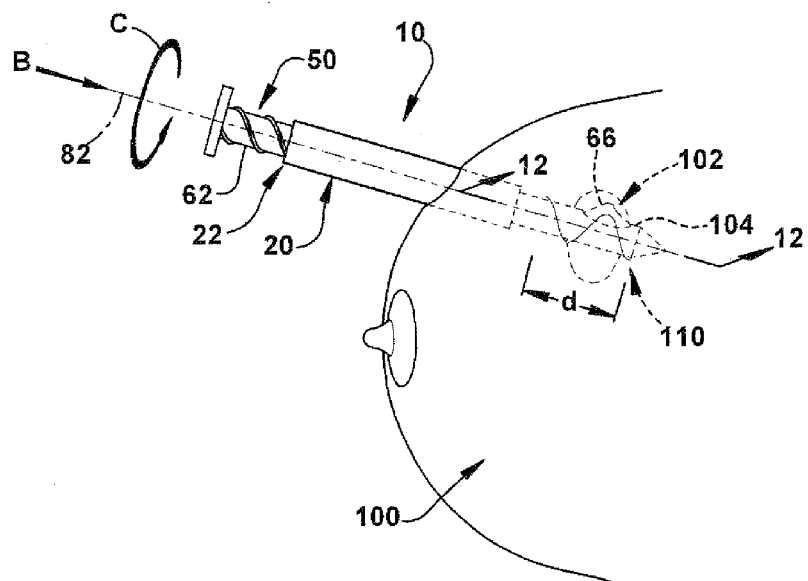
FIG. 11 is a schematic illustration of the device obtaining a tissue sample.
Figure 12:
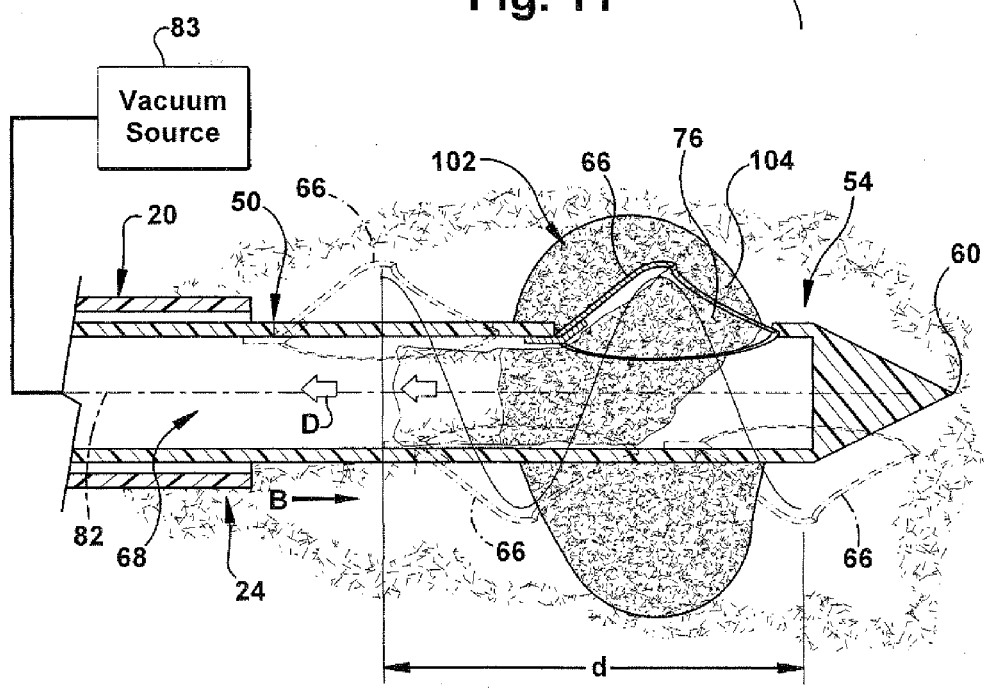
FIG. 12 is a section view of the device taken along line 12-12 in FIG. 11.

In order to obtain a tissue sample 104 within the target area 102 following extension of the cutting needle 66, the handle 62 on the inner tube 50 is further rotated in the direction indicated at C to further engage the threads 64 on the inner tube with the threads 38 on the sheath 20 (FIG. 11). As shown in FIGS. 11-12, since the sheath 20 is fixed in position relative to the inner tube 50, this rotation of the inner tube causes the extended cutting needle 66 to rotate about the central axis 82 while advancing into the tissue 102 in the direction indicated at B. This simultaneous rotational and translational movement of the cutting needle 66 causes the cutting needle to follow a helical path 110 in the target area 102 about the central axis 82 (FIG. 12). Since the cutting needle 66 is in contact with the breast tissue in the target area 102, the cutting needle cuts and removes the tissue it comes into contact with along that helical path 110. It is this severed tissue that constitutes the desired tissue sample 104.

As the tissue sample 104 is collected, the sample enters the aperture 76 of the cutting needle 66, then the passage 68 of the inner tube 50, and subsequently travels toward the first end 52 of the inner tube, as indicated by "D" (FIG. 12). The tissue sample 104 may be drawn into the passage 68 of the inner tube 50 under natural reaction forces due to the advancement of the inner tube along the axis 82 or under the assistance of a vacuum source 83 applied to the opening 70 at the first end 52 of the inner tube to draw the tissue into the passage.

As noted, the cross-section of the tissue sample 104 taken is based on the size and shape of the cutting needle 66 as well as the extent to which the cutting member extends radially beyond the outer surface 58 of the inner tube 50. That cross-section of the tissue sample 104 is cut to a depth, illustrated by "d". The depth "d" is dependent upon the type of tissue sample 104 taken, the location of the sample within the body, and the clinical and/or diagnostic applications. By obtaining the tissue sample 104 along a helical path 110, the tissue sample obtained is much longer than that obtained with a conventional straight throw or straight cutting path biopsy device over the same cutting depth. Accordingly, the volume of the tissue sample 104 removed by the device 10 of the present invention is greater than the tissue volume obtained with conventional biopsy devices. This increased tissue sample 104 volume allows for greater diagnostic accuracy in that a more contiguous tissue sample and/or a broader distribution of sampling may be obtained. The increased tissue sample 104 volume also results in a faster procedure in that only one pass is required—as opposed to multiple passes required by conventional biopsy devices—to capture an adequate tissue volume for testing.

Figure 13:
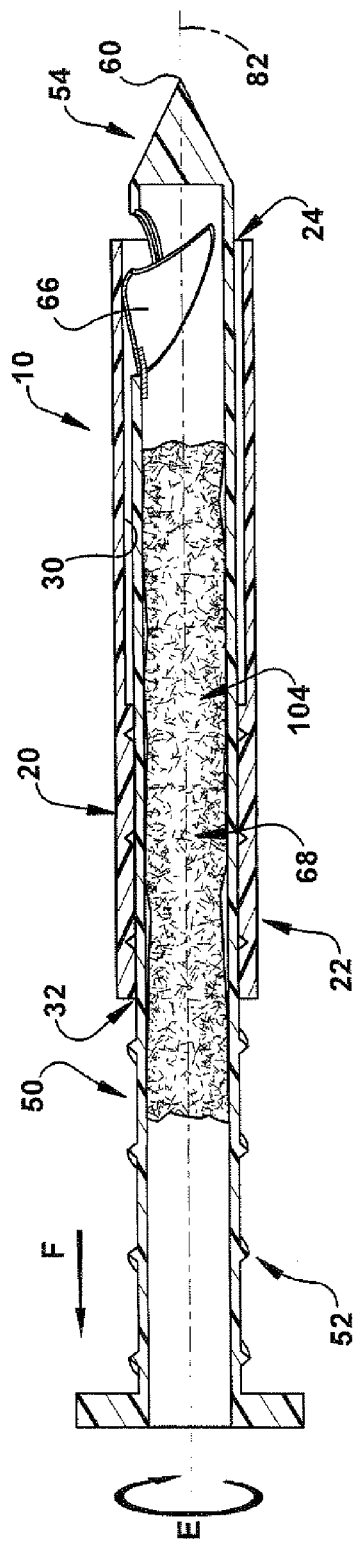
FIG. 13 is a side view of the device of FIG. 12 following tissue sampling.

Once the desired depth "d" of the tissue sample 104 is obtained and the sample disposed within the passage 68 of the inner tube 50, the handle 62 on the inner tube is rotated in the counterclockwise direction as indicated by "E" (FIG. 13) relative to the sheath 20 such that the second end 54 of the inner tube moves along the central axis 82 and back towards the proximal end 22 of the sheath, as indicated by "F". Additional rotation of the handle 62 causes the inner surface 36 of the sheath 20 to contact the portion 80 of the cutting needle 66 and reapply the radially inward force to the cutting needle. This radially inward force causes the cutting needle 66 to pivot back toward the central axis 82 and into the retracted position radially inward of the inner surface 36. When the cutting needle 66 pivots radially inward as the sheath 20 covers the opening 74, the tissue sample 104 is severed from the in vivo breast tissue and the opening and, thus, the passage 68, is sealed off from the surrounding tissue. This retraction of the inner tube 50 relative to the sheath 20 therefore isolates the tissue sample 104 from the breast 100 and secures the tissue sample 104 within the passage 68 of the inner tube. Although the inner tube 50 is retracted relative to the sheath 20 in order to reposition the inner surface 36 of the sheath over the cutting needle 66 and, thus, place the cutting needle in the retracted position, the inner tube remains threadably engaged with the sheath to prevent sliding movement of the inner tube relative to the sheath.

By placing the cutting needle 66 in the retracted position, the device 10 is also configured for safe and easy withdrawal from the breast 100. When the cutting needle 66 is in the retracted position, the sheath 20 prevents the cutting needle from further cutting the breast tissue. Therefore, due to the threaded engagement between the sheath 20 and the inner tube 50, pulling the handle 62 on the inner tube will cause the sheath and the inner tube to move out of, and ultimately exit, the breast 100. Accordingly, when the practitioner pulls on the handle 62 on the first end 52 of the inner tube 50 along the central axis 82 and away from the breast 100 (not shown) the device 10 can be readily removed from the target area 102 and the breast without the risk of the cutting needle 66 unnecessarily cutting breast tissue, i.e., tissue outside of the target area 102. The present invention therefore provides for a one pass biopsy device that effectively removes targeted breast tissue without risking collateral damage to surrounding tissue during removal of the device.

Although the device 10 is illustrated as relying on a threaded engagement between the sheath 20 and the inner tube 50, those having ordinary skill will appreciate that the device could likewise function without threads of any kind. For example, the sheath 20 and the inner tube 50 may be manually slidable relative to one another—but not threadably engaged—to pivot the cutting needle 60 between the extended and retracted positions as discussed. Furthermore, instead of using a threaded engagement between the sheath 20 and the inner tube 50, the practitioner may manually move the sheath with and/or relative to the inner tube in order to both remove the tissue sample along the helical path and remove the device without removing tissue outside of the target area.

Another embodiment of a tissue sampling device 10a in accordance with the present invention is illustrated in FIGS. 14-15. The tissue sampling device 10a is identical to the tissue sampling device 10 illustrated in FIGS. 1-13, except as described below. In FIGS. 14-15, structures that are identical as structures in FIGS. 1-13 use the same reference numbers, whereas structures that are similar but not identical carry the suffix "a".

In this embodiment, the depth "d" of the tissue sample 104 can be monitored by the use of an adjustable nut 114. The nut 114 is threadably engaged with the threads 64 on the outer surface 58 of the inner tube 50a and limits longitudinal movement of the inner tube relative to the sheath 20a. As with the device 10, the insertion of the device 10a into the breast causes the proximal end 22 of the sheath 20a to abut the threads 64 on the inner tube 50a. The body portion 26a of the sheath 20a, however, is sized such that when the proximal end 22 of the sheath abuts the threads on the inner tube 50a, the inner surface 36 at the distal end 24 of the sheath 20a does not overlie or contact the cutting member 66 (not shown). This construction therefore places the cutting member 66 in the extended position without a threaded engagement between the inner tube 50a and the sheath 20a. Those having ordinary skill in the art, however, will appreciate that the device 10a may be constructed such that the cutting needle 60 does not move to the extended position until a predetermined number of threads 64 on the inner surface 36 of the inner tube 50a engage the threads 38 on the sheath 20a (not shown).

The handle 62 on the inner tube 50 is then rotated in the direction indicated at C to engage the threads 64 on the inner tube with the threads 38 on the sheath 20a. This rotation causes the cutting needle 66 to rotate about the central axis 82 while advancing into the target area 102 in the direction indicated at B. As the inner tube 50a is rotated and advanced to cut the tissue with the cutting needle 66 along the helical path, the first end 52 of the inner tube and, thus, the nut 114 threadably engaged with the threads 64 on the first end 52 move in the direction indicated at B closer to the proximal end 22 of the sheath 20a. The nut 114 eventually abuts the proximal end 22 of the sheath 20a, prohibiting further movement of the inner tube 50a relative to the sheath and, thus, further rotational and translational movement of the cutting needle 66 into the tissue.

The distance between the nut 114 and the first thread 64 on the inner tube 50a that engages the threads 38 on the sheath 20a is indicated by "t" (FIG. 14). Since the cutting member 66 does not move to the extended position until the proximal end 22 of the sheath 20a abuts the threads 64 on the inner tube 50a, the distance indicated at "t" corresponds to the depth "d" of the tissue sample 104 that will be cut (see FIG. 12). The depth "d" of the sample 104 is therefore directly correlative to the amount of threaded engagement between the inner tube 50a and the sheath 20a. In particular, by limiting the amount of thread engagement between the sheath 20a and the inner tube 50a, the depth "d" of the tissue sample 104 is also minimized. Likewise, maximizing the amount of thread engagement between the sheath 20a and the inner tube 50a also maximizes the depth "d" of the tissue sample 104 taken. Accordingly, by changing the longitudinal position of the nut 114 along the threads 64 and, thus, the extent to which the inner tube 50a can threadably engage the sheath 20a, the practitioner is capable of pre-selecting the desired depth "d" of the tissue sample 104 to be taken based on anatomic conditions, diagnostics, clinical indications, etc.

In order to accurately monitor the distance "t" and, thus, the depth "d" of the tissue sample 104, a portion of the threads 64 on the inner tube 50a may be machined or otherwise adapted to bear indicia 108 (FIG. 15). The indicia 108 may constitute incremental measurements such as, for example, inches, centimeters, millimeters, etc. By utilizing the nut 114 and indicia 108, the device 10a may be safer than conventional biopsy devices in that the depth "d" of the tissue sample cut can be adjusted so that only abnormal or desired tissue is extracted, leaving otherwise healthy tissue intact.

Although a nut 114 is illustrated to adjust the depth "d" of the tissue sample 104, it will be understood that alternative means may be utilized to allow the user of the device 10a to monitor the tissue depth. This may include, but is not limited to, a viewing window on the sheath 20a bearing indicia, multiple inner tubes 50a bearing preset lengths of threads in a kit, or the like.

Another embodiment of a tissue sampling device 10b in accordance with the present invention is illustrated in FIG. 16. The tissue sampling device 10b is identical to the tissue sampling device 10 illustrated in FIGS. 1-13, except as described below. In FIG. 16, structures that are identical as structures in FIGS. 1-13 use the same reference numbers, whereas structures that are similar but not identical carry the suffix "b".

In this embodiment, the first end 52 of the inner tube 50b is threadably engaged with an external driver, illustrated schematically at 120. The external driver 120 is powered via electric cable 122 to rotate the inner tube 50b about the central axis 82 in the manner indicated at "C" and, thus, rotate the second end 54 of the inner tube 50b bearing the cutting needle 66. Furthermore, in this embodiment of the device 10b the inner tube 50b does not threadably engage the sheath 20b. Rather, the sheath 20b is slidably disposed on the inner tube 50b to allow the inner surface 36 of the sheath to longitudinally translate across the outer surface 58 of the inner tube in the directions indicated at "G" to selectively cause the cutting needle 66 to pivot between the extended and retracted positions. Those having ordinary skill in the art will appreciate that the proximal end 22 of the sheath 20b may be provided with threads in order to secure the sheath 20b to the inner tube 50b, if necessary.

In use, the device 10b is inserted into the tissue 100 proximate the target area 102 as discussed above, with the sheath 20b disposed at the second end 54 of the inner tube 50b such that the inner surface 36 of the sheath overlies the cutting needle 66 and thereby maintains the cutting needle in the retracted position. If necessary, the practitioner may hold the sheath 20b and the inner tube 50b together to ensure that the inner surface 36 of the sheath maintains an overlying position over the cutting needle 66 during insertion into the breast 100. Once the second end 54 of the inner tube 50b reaches the target area 102, the sheath 20b is retracted back towards the first end 52 of the inner tube opposite the direction indicated by "B" by applying a translational force to the sheath. This displaces the inner surface 36 of the sheath 20b from the cutting needle 66 and allows the cutting needle to move into the extended position. The external driver 120 is then energized to rotate the inner tube 50b via the threaded engagement between the two.

Simultaneously, the external driver 120 is grasped via a handle 121 or the like and advanced into the target area 102 of the breast 100. Alternatively, the external driver 120 may be adapted to both rotate and advance the inner tube 50b in the manner indicated at B while the handle 121 is held stationary. Regardless, this combination of rotational and translational movement of the inner tube 50b causes the cutting needle 66 to cut the tissue along the helical path and capture the tissue. Once the tissue sample has been obtained, the driver 120 is de-energized and the sheath 20b is moved back over the second end 54 of inner tube 50b to return the inner surface 36 of the sheath to a position overlying the cutting needle 66 and, thus, place the cutting needle back into the retracted position. A portion of the second end 54 of the inner tube 50b may include a stop or other means (not shown) to prohibit the sheath 20b from sliding completely off the second end of the inner tube when the sheath is moved towards the second end of the inner tube. The device 10b can then be removed from the tissue with the sample intact.

From the above description of the invention, those skilled in the art will perceive improvements, changes and modifications. Such improvements, changes and modifications within the skill of the art are intended to be covered by the appended claims.

Having described the invention, the following is claimed:

1. A tissue sampling device for removing tissue from a target area in the body comprising:
   a sheath having a proximal end, a distal end, and an inner surface extending between the proximal end and the distal end and defining a passage;
   an inner tube disposed within the passage of the sheath, the inner tube having a first end, a second end, an inner surface extending between the first end and the second end and defining a passage, and an outer surface spaced radially outward from the inner surface; and
   a cutting needle pivotally mounted to the inner tube, the cutting needle being pivotable between a first position radially inward of the inner surface of the sheath and extending into the passage of the inner tube and a second position extending radially outward of the inner surface of the sheath;
   wherein relative movement between the inner tube and the sheath causes the cutting needle to move between the first position and the second position,
   wherein rotation of the inner tube relative to the sheath when the cutting needle is in the second position causes the cutting needle to remove tissue from the target area in a helical path.

2. The device recited in claim 1, wherein the inner tube includes a lateral aperture extending from the outer surface of the inner tube to the inner surface of the inner tube, the cutting needle being positioned in the lateral aperture.

3. The device recited in claim 1, wherein the sheath applies a radially inward force to the cutting needle to maintain the cutting needle in the first position, the sheath applying no force upon the cutting needle when the cutting needle is in the second position.

4. The device recited in claim 1, wherein the inner surface of the sheath and the outer surface of the inner tube each have threads formed thereon, the threads on the inner tube configured to releasably engage the threads on the sheath.

5. The device recited in claim 4, wherein rotation of the inner tube relative to the sheath causes the cutting needle to move between the first position and the second position.

6. The device recited in claim 4, wherein a depth of the tissue removed by the cutting needle is equal to the extent of the threaded engagement between the inner tube and the sheath.

7. The device recited in claim 4, wherein a nut secured to the threads of the inner tube is adjustable to limit the extent to which the inner tube and the sheath can threadably engage one another.

8. The device recited in claim 7, wherein indicia on the threads of the inner tube indicate the extent to which the inner tube and the sheath can be threadably engaged to one another.

9. The device recited in claim 1, wherein the cutting needle is provided with an aperture to receive the removed tissue.

10. The device recited in claim 9, wherein the aperture of the cutting needle is in fluid communication with the passage of the inner tube, the removed tissue being drawn through the aperture and into the passage of the inner tube.

11. The device recited in claim 9, wherein the aperture in the cutting needle is configured to receive a vacuum pressure to draw the tissue into the aperture.

12. The device recited in claim 1, wherein an external driver is engageable and rotatable with the inner tube to cut the tissue in a helical path.

13. The device recited in claim 1, wherein the cutting needle is secured to the inner surface of the inner tube by a hinge, the cutting needle being pivotable about the hinge between the first position and the second position.

14. A method of tissue sampling from a target area in the body, the method comprising the steps of:
provides a sheath having a proximal end, a distal end, and an inner surface extending between the proximal end and the distal end and defining a passage;
providing an inner tube within the passage of the sheath, the inner tube having a first end, a second end, an inner surface extending between the first end and the second end and defining a passage, and an outer surface spaced radially outward from the inner surface, wherein a cutting needle is pivotally mounted to the inner tube, the cutting needle pivoting between a first position and a second position, the first position being radially inward of the inner surface of the sheath and extending into the passage of the inner tube and the second position extending radially outward of the inner surface of the sheath;
sliding the sheath relative to the inner tube such that the cutting needle pivots from the first position to the second position; and
removing tissue from the target area along a helical path by rotating the inner tube relative to the sheath when the cutting needle is in the second position.

15. The method recited in claim 14, wherein the step of sliding the sheath includes rotating the inner tube relative to the sheath in order to slide the sheath relative to the inner tube.

16. The method of claim 14 further comprising a step of providing threads on the inner surface of the sheath that are releaseably engageable with threads on the outer surface of the inner tube.

17. The method of claim 16 further comprising a step of limiting the extent to which the inner tube is threadably engaged with the sheath by providing a nut on the threads of the inner tube.

18. The method recited in claim 14, wherein the step of removing tissue along a helical path includes rotating the inner tube with an external driver.

19. The method recited in claim 14 further comprising the step of sliding the sheath relative to the inner tube to pivot the cutting needle from the second position to the first position to secure the tissue sample in the passage of the inner tube.

20. The method recited in claim 14 further comprising securing the cutting needle to the inner surface of the inner tube by a hinge such that the cutting needle pivots about the hinge between the first position and the second position.

* * * * *